US00PP09842P

United States Patent [19]

Zaiger et al.

[11] Patent Number: Plant 9,842

[45] Date of Patent: Apr. 1, 1997

[54] PEACH TREE 'EARLITREAT'

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesta, Calif. 95358

[21] Appl. No.: 523,532

[22] Filed: Sep. 5, 1995

[51] Int. Cl.[6] ..... A01H 5/00

[52] U.S. Cl. ..... Plt./43.1

[58] Field of Search ..... Plt./42.1, 43.1

*Primary Examiner*—James R. Feyrer

[57] ABSTRACT

A new and distinct variety of peach tree which has the unique combination of outstanding features that are desirable in a new variety:

1. Fruit with good flavor and eating quality.
2. Early maturity of its fruit.
3. Fruit with good handling and shipping quality.
4. Having a low winter chilling requirement of approximately 350 hours.
5. Heavy and regular production of fruit.
6. Fruit having yellow ground color with an attractive red blush.
7. Vigorous upright growth.

1 Drawing Sheet

ORIGIN OF THE VARIETY

The present new and distinct variety of peach tree was originated by us in our experimental orchard located near Modesto, Calif. as a first generation cross between a selected seedling with the field identification number of 12ED34 and Sweet Gem Peach (U.S. Plant Pat. No. 7,952). The maternal parent with the field identification number 12ED34 originated from a cross between the selected seedling 27GA575 and May Crest Peach (U.S. Plant Pat. No. 4,064). The selected seedling 27GA575 originated from a seedling selection of open pollinated Red Grand Nectarine (U.S. Plant Pat. No. 1,060) crossed with Desert Gold Peach (non-patented). We grew and maintained these first generation seedlings under close observation, during which time one such early maturing seedling, which is the present variety, having especially desirable fruit characteristics was selected for asexual reproduction and commercialization.

ASEXUAL REPRODUCTION OF THE VARIETY

The present new variety of peach tree was asexually reproduced by budding, as performed by us in our experimental orchard located near Modesto, Calif. and shows all characteristics of the tree and its fruit are established and transmitted through succeeding asexual reproductions and come true to the original tree in all respects.

SUMMARY OF THE VARIETY

The new and distinct variety of peach tree is of large size, vigorous, upright in growth and is a productive and regular bearer of medium size, early maturing, yellow flesh, clingstone fruit with good flavor and eating quality. The fruit is further characterized by having firm flesh with good handling and shipping quality, having an attractive red blush and in comparison to May Crest Peach (U.S. Plant Pat. No. 4,064), has a lower winter chilling requirement and is approximately 14 days earlier in maturity.

PHOTOGRAPH OF THE VARIETY

The accompanying color photographic reproduction show typical specimens of the foliage and fruit of the present new peach tree. The upper and lower surface of the leaves being illustrated with specimens of the fruit showing the exterior skin color. The photograph was taken shortly after the fruit had been picked (shipping ripe) and the colors are as nearly true as is reasonably possible in a color representation of this type.

DESCRIPTION OF THE VARIETY

The following botanical details of the present new and distinct variety of peach tree, its flowers, foliage and fruit are based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Productivity.*—Productive.
- *Bearing.*—Regular.

Trunk:
- *Size.*—Large.
- *Texture.*—Medium shaggy.
- *Color.*—Light brown to grayish brown (5-E-5) to (5-F-5).

Branches:
- *Size.*—Medium.
- *Texture.*—Smooth to medium rough. Varies with age of growth.
- *Lenticels.*—Numerous. Large size.
- *Color.*—Light brown to brown (5-D-7) to (5-D-8).

Leaves:
- *Size.*—Large. Average length 7½". Average width 1½".
- *Form.*—Lanceolate. Pointed.
- *Thickness.*—Medium.
- *Margin.*—Crenate.
- *Texture.*—Smooth.
- *Petiole.*—Medium length. Medium thickness.
- *Glands.*—Reniform. Number varies from 1 to 5. Average number 3. Located on base of leaf blade and on upper portion of petiole.
- *Color.*—Upper surface — green to dark green (28-F-6) to (28-F-8). Lower surface — dull green to green (28-E-5) to (28-E-6).

Flower buds:
- *Size.*—Medium to large.
- *Form.*—Plump.
- *Pubescence.*—Pubescent.

Flowers:

*Size.*—Large — showy.

*Blooming period.*—Feb. 20, 1993 to Feb. 28, 1993. Varies slightly with climatic conditions.

*Pollen.*—Present — self fertile.

*Color.*—Pink.

Fruit:

*Maturity when described.*—Firm ripe.

*Date of first picking.*—Apr. 30, 1993.

*Date of last picking.*—May 5, 1993.

*Size.*—Medium. Average diameter axially 2½". Average transversely in suture plane 2½".

*Form.*—Globose — slightly flattened at stem end.

*Suture.*—Shallow — but pronounced, extends from base to apex.

*Ventral surface.*—Nearly round.

*Cavity.*—Rounded to elongated in suture plane.

*Base.*—Retuse.

*Apex.*—Varies from round to slight point.

Flesh:

*Ripens.*—Relatively even.

*Texture.*—Firm.

*Juice.*—Moderate.

*Flavor.*—Mild — good balance between sugar and acid.

*Aroma.*—Moderate.

*Eating quality.*—Good.

*Fibers.*—Few, small, tender.

*Amygdalin.*—Undetected.

*Color.*—Yellow to butter yellow (4-A-5) to (4-A-7). Pit cavity — yellow (4-A-5).

Skin:

*Thickness.*—Medium.

*Texture.*—Medium — tenacious to flesh.

*Tendency to crack.*—None.

*Down.*—Moderate amount. Short in length.

*Color.*—Yellow ground color — light yellow to yellow (3-A-4) to (3-A-6). Red blush color — lake red to red (9-C-8) to (9-D-8).

Stone:

*Type.*—Clingstone.

*Size.*—Medium. Average length 1¼". Average width 1". Average thickness ½".

*Form.*—Obovate.

*Base.*—Usually straight varies from round to straight.

*Apex.*—Cuspidate.

*Surface.*—Irregularly furrowed toward apex, pitted toward base.

*Ridges.*—Rounded.

*Sides.*—Mostly equal, varies from equal to unequal.

*Tendency to split.*—Very slight.

*Color.*—Light tan to light brown (4-B-5) to (4-C-5).

Use: Dessert.

*Market.*—local and long distance.

Keeping quality: Good.

Shipping quality: Good.

The present variety of peach tree, its flowers, foliage and fruit herein described may vary in slight detail due to climate, soil conditions and cultural practuces under which the variety may be grown, the present description is that of the variety grown under the ecological conditions prevailing near Modesto, Calif.

We claim:

1. A new and distinct variety of peach tree, substantially as illustrated and described, which is of large size, vigorous, upright in growth and a productive and regular bearer of early maturing, yellow flesh, clingstone fruit with good flavor and eating quality, the fruit is further characterized by having an attractive red blush, having firm flesh with good handling and shipping quality and in comparison to May Crest Peach (U.S. Plant Pat. No. 4,064) the new variety requires less winter chilling and the fruit is approximately 14 days earlier in maturity.

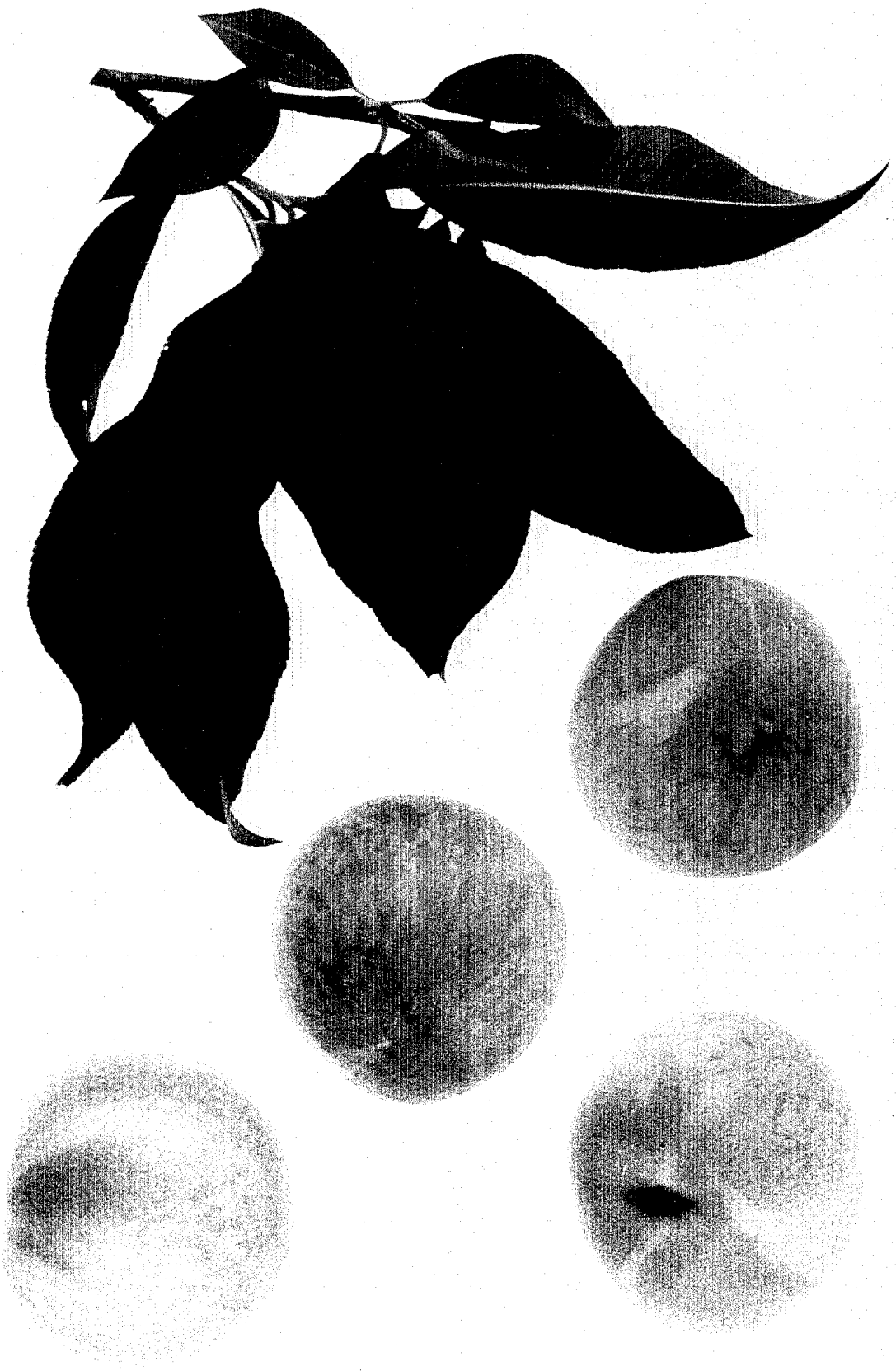

* * * * *